United States Patent
Rhazi

(10) Patent No.: US 11,300,497 B2
(45) Date of Patent: Apr. 12, 2022

(54) SYSTEM, ELECTRODE AND METHOD FOR EVALUATING A CONDITION OF STEEL REINFORCEMENTS IN CONCRETE

(71) Applicant: AUSCULTECH INC., Sherbrooke (CA)

(72) Inventor: Jamal-Eddine Rhazi, Sherbrooke (CA)

(73) Assignee: AUSCULTECH INC., Sherbrooke (CA)

( * ) Notice: Subject to any disclaimer, the term of this patent is extended or adjusted under 35 U.S.C. 154(b) by 160 days.

(21) Appl. No.: 16/867,810

(22) Filed: May 6, 2020

(65) Prior Publication Data
US 2020/0264092 A1 Aug. 20, 2020

Related U.S. Application Data

(63) Continuation of application No. PCT/CA2018/051395, filed on Nov. 5, 2018.
(Continued)

(51) Int. Cl.
*G01R 27/08* (2006.01)
*G01N 17/02* (2006.01)
(Continued)

(52) U.S. Cl.
CPC ........... *G01N 17/02* (2013.01); *G01N 17/006* (2013.01); *G01N 33/383* (2013.01); *G01R 19/10* (2013.01)

(58) Field of Classification Search
CPC .... G01N 17/02; G01N 17/006; G01N 33/383; G01R 19/10
(Continued)

(56) References Cited

U.S. PATENT DOCUMENTS 2,974,276 A 3/1961 Davis
3,806,795 A 4/1974 Morey
(Continued)

FOREIGN PATENT DOCUMENTS

CN 2872355 Y 2/2007
EP 0216628 A2 4/1987
(Continued)

OTHER PUBLICATIONS

Song et al., Corrosion Monitoring of Reinforced Concrete Structures—A Review, International Journal of Electrochemical Science, vol. 2, pp. 1-28, 2007.
(Continued)

*Primary Examiner* — Raul J Rios Russo
(74) *Attorney, Agent, or Firm* — BCF LLP

(57) ABSTRACT

The present disclosure relates to a method, system and electrode for evaluating a condition of steel reinforcements in concrete structures. A reference electrode is positioned on a first area on a concrete structure. An electromagnetic survey is performed to estimate a reference voltage for the reference electrode. A measurement electrode is positioned on a second area on the concrete structure. A difference of potential between the reference electrode and the measurement electrode is determined. A voltage at the measurement electrode is determined based on the reference voltage and on the difference of potential. A corrosion probability at the second area is determined based on the voltage at the measurement electrode. Several electrodes may be placed in an array. Any one of the electrodes may be moved to various areas on the concrete structure.

21 Claims, 15 Drawing Sheets

Related U.S. Application Data

(60) Provisional application No. 62/582,133, filed on Nov. 6, 2017.

(51) Int. Cl.
    G01N 17/00     (2006.01)
    G01N 33/38     (2006.01)
    G01R 19/10     (2006.01)

(58) Field of Classification Search
USPC .......... 324/76.11–76.83, 459, 600, 649, 691, 324/693, 699, 700
See application file for complete search history.

(56) References Cited

U.S. PATENT DOCUMENTS

| | | |
|---|---|---|
| 3,831,173 A | 8/1974 | Lerner |
| 4,072,942 A | 2/1978 | Alongi |
| 4,388,594 A | 6/1983 | Ashbaugh et al. |
| 4,414,511 A | 11/1983 | Bushman et al. |
| 4,584,530 A | 4/1986 | Nicholson et al. |
| 4,623,434 A | 11/1986 | Nicholson et al. |
| 4,698,634 A | 10/1987 | Alongi et al. |
| 4,706,031 A | 11/1987 | Michiguchi et al. |
| 4,758,324 A | 7/1988 | Winneti et al. |
| 4,806,850 A | 2/1989 | Saumade et al. |
| 4,896,116 A | 1/1990 | Nagashima et al. |
| 4,927,503 A | 5/1990 | Polly |
| 4,942,354 A | 7/1990 | Miller |
| 5,180,969 A | 1/1993 | Kwun et al. |
| 6,429,802 B1 | 8/2002 | Roberts |
| 7,446,522 B2 | 11/2008 | Sedlet |
| 8,778,167 B2 | 7/2014 | Raupach et al. |
| 9,073,347 B2 | 7/2015 | Feigin |
| 9,194,819 B2 | 11/2015 | Bulumulla et al. |
| 2003/0169058 A1* | 9/2003 | Pierre ............ C23F 13/04 324/700 |
| 2004/0123665 A1 | 7/2004 | Blodgett et al. |
| 2012/0080325 A1* | 4/2012 | Raupach ............ G01N 17/02 205/776.5 |
| 2012/0280849 A1 | 11/2012 | Chang et al. |
| 2012/0286804 A1 | 11/2012 | Kato et al. |
| 2014/0210494 A1 | 7/2014 | Ghods et al. |
| 2015/0362422 A1 | 12/2015 | Mazzeo et al. |
| 2018/0238820 A1* | 8/2018 | Ghods ............ G01N 17/02 |

FOREIGN PATENT DOCUMENTS

| | | |
|---|---|---|
| EP | 0259253 A2 | 8/1988 |
| EP | 0354096 A1 | 2/1990 |
| EP | 0199867 B1 | 8/1990 |
| EP | 2653864 A1 | 10/2013 |
| GB | 2157441 A | 10/1985 |
| WO | 2009007395 A1 | 1/2009 |

OTHER PUBLICATIONS

Travassos, Numerical modeling for the electromagnetic non-destructive evaluation: Application to the non-destructive evaluation of concrete, Ecole Centrale de Lyon, 2007, pp. 1-134.

International Search Report and Written Opinion issued in corresponding International application No. PCT/CA2018/051395 dated Jan. 31, 2019.

ASTM, Standard Test Method for Corrosion Potentials of Uncoated Reinforcing Steel in Concrete, 2013.

ASTM, Standard Test Method for Evaluating Asphalt-Covered Concrete Bridge Decks Using Ground Penetrating Radar, 2008.

Broomfield et al., The Use of a Potential Wheek to Survey Reinforced Concrete Structures, Corrosion Rates of Steel in Concrete, ASTM STP 1065,1990, pp. 157-173.

Elsener et al., Half-cell potential measurements—Potential mapping on reinforced concrete structures, Materials and Structures, vol. 36, pp. 461-471, 2003.

Elsener et al., Climbing robot for corrosion inspection and monitoring of reinforced and post-tensioned concrete structures, 2014.

Grdic et al., Nondestructive methods for determination of reinforcement steel corrosion in concrete, Zastita Materijala 54, broj 3, pp. 207-215, 2013.

Helal et al., Non-Destructive Testing of Concrete: A Review of Methods, Special Issue: Electronic Journal of Structural Engineering 14(1), pp. 97-105, 2015.

Lai et al., Measurement of accelerated steel corrosion in concrete using ground-penetrating radar and a modified half-cell potential method, Journal of Infrastructure Systems, 19:205-220, 2013.

MacDonald et al., Evaluation of electrochemical impedance techniques for detecting corrosion on rebar in reinforced concrete, Strategic Highway Research Program, National Research Council, Washington DC, 1994.

Sagues, Corrosion measurement techniques for steel in concrete, The NACE Annual Conference and Corrosion Show, Paper No. 353, 1993.

Singh et al., Developments in Corrosion Detection Techniques for Reinforced Concrete Structures, Indian Journal of Science and Technology, vol. 9(30), 2016.

Skolnik, Chapter 1: An Introduction to Radar, Radar Handbook, p. 1.1-1.21.

Tullmin et al., Electrochemical techniques for measuring reinforcing steel corrosion, 2008.

Verma et al., Monitoring Corrosion of Steel Bars in Reinforced Concrete Structures, The Scientific World Journal, vol. 2014, pp. 1-9, 2014.

Wilcox, Team tests robot in bridge inspections, Civil Engineering The Magazine of the American Society of Civil Engineers, 2017.

Zaki et al., Non-Destructive Evaluation for Corrosion Monitoring in Concrete: A Review and Capability of Acoustic Emission Technique, Sensors , vol. 15, p. 19069-19101, 2015.

\* cited by examiner

600

- 604 — Position a reference electrode on a first area on a surface of a concrete structure
- 606 — Perform an electromagnetic survey at the first area to estimate a reference voltage for the reference electrode
- 608 — Position a measurement electrode on a second area of the concrete structure
- 610 — Determine a difference of potential between the reference electrode and the measurement electrode
- 612 — Determine a voltage at the measurement electrode based on the reference voltage and on the difference of potential
- 614 — Determine a corrosion probability at the second area based on the voltage at the measurement electrode
- 616 — Reposition the measurement electrode to successive additional areas
- 618 — Determine successive differences of potential between the reference electrode and the measurement electrode at each of the successive additional areas
- 620 — Determine successive voltages at the measurement electrode based on the reference voltage and on the successive differences of potential
- 622 — Determine a corresponding corrosion probability at each of the successive additional areas based on a corresponding voltage at the measurement electrode

Figure 12

SYSTEM, ELECTRODE AND METHOD FOR EVALUATING A CONDITION OF STEEL REINFORCEMENTS IN CONCRETE

CROSS-REFERENCE

The present application is a continuation of International Patent Application No. PCT/CA2018/051395 filed on Nov. 5, 2018, which claims priority from U.S. Provisional Application No. 62/582,133 filed on Nov. 6, 2017, the entirety of both of which is incorporated by reference herein.

TECHNICAL FIELD

The present disclosure relates to the field of non-destructive testing of concrete structures. More specifically, the present disclosure relates to a method, an electrode and a system for evaluating a condition of steel reinforcements in concrete.

BACKGROUND

Concrete is the most widely used material in the world for the construction of civil engineering infrastructures. This material generally contains steel reinforcement in the form of reinforcing bars (oftentimes called "rebars"), cables or anchors. This reinforcement play a very important role in the mechanical behavior of reinforced concrete structures such as bridge decks, parking garage slab floors, tunnel linings, pavements, etc.

Corrosion of steel reinforcement is the main cause of degradation of reinforced concrete bridge decks and slab floors of parking garages. This corrosion is frequently due to the infiltration of chloride ions dissolved in water into the concrete through the pores and the micro-cracks in it. These chloride ions are mainly derived from de-icing salts used for the winter maintenance of structures. They can also be contained in the atmosphere when structures are located on the seafront.

The corrosion of the steel reinforcement in reinforced concrete such as bridge decks and parking garage slab floors leads to the dissolution of these elements. This weakens these structures and makes them less able to withstand high loads. They can no longer be operated at their full capacity and can even be taken out of service if they become unsafe. In addition, the product of corrosion (rust) creates cracks in the concrete and these cracks further weaken the structural capacity of these structures and contribute to their collapse. Corrosion damage to reinforced concrete structures such as reinforced concrete bridge decks and parking garage slab floors is costly in terms of human life, detrimental to the environment and disrupting economic activity.

Test methods for determining the state of corrosion of steel reinforcement in reinforced concrete structures are therefore extremely important for a better management of these structures. The cost of maintenance car be reduced and durability of these structures can be significantly increased.

The most direct method for determining the state of corrosion of steel reinforcement in reinforced concrete bridge decks and parking garage slab floors consists in taking a small number of samples of steel reinforcement by coring and subjecting them to visual analysis. This method is destructive and the results are restricted to areas where coring has been carried out; typically 1% of the total surface of a reinforced concrete slab. Other test methods have been developed to overcome these limitations.

A commonly used technique worldwide for obtaining information on corrosion activity of reinforcing steel in concrete is the half-cell potential technique. This test method is described in ASTM C876—*Standard Test Method for Corrosion Potentials of Uncoated Reinforcing Steel in Concrete*. It consists in measuring the electrical potential difference between the reinforcing steel in concrete and a reference electrode in contact with the concrete surface. This test method has several significant disadvantages. Indeed, for example, in most cases, the upper surface of reinforced concrete bridge decks and slab floor of parking garages are covered with a bituminous layer to protect them against the infiltration of ions chloride. This bituminous layer must be perforated at each measuring point to establish the electrical contact between the measuring electrode and the concrete surface. In addition, a coring must be done in the concrete to establish the electrical contact between steel reinforcement and the measuring device (voltmeter). These perforations and coring may impact the efficiency of the bituminous layer. Furthermore, this technique requires that all the reinforcements in the slab be interconnected to ensure electrical continuity between them; which is not always satisfied. Finally, this test method also requires the closure of traffic lanes during data collection. This is very problematic in large urban areas. For all these reasons, structural engineers are looking since several years for alternative nondestructive testing techniques to evaluate corrosion of steel in reinforced concrete elements such as bridge deck and slab floor of parking garages.

Therefore, there is a need for improved non-destructive techniques for determining the state of corrosion of steel reinforcement in reinforced concrete.

SUMMARY

According to a first aspect of the present disclosure, there is provided a method for evaluating a condition of steel reinforcements in a concrete structure. A reference electrode is positioned on a first area on concrete structure. An electromagnetic survey is performed at the first area to estimate a reference voltage for the reference electrode. A measurement electrode is positioned on a second area on the concrete structure. A difference of potential between the reference electrode and the measurement electrode is determined. A voltage at the measurement electrode is determined based on the reference voltage and on the difference of potential. A corrosion probability at the second area is determined based on the voltage at the measurement electrode.

According to a second aspect of the present disclosure, there is provided a method for evaluating a condition of steel reinforcements in concrete. An array of electrodes is positioned at a first location on a concrete structure, the array of electrodes including a reference electrode and a plurality of measurement electrodes. An electromagnetic survey is performed to estimate a first reference voltage at an area of contact between the reference electrode and the concrete structure. For each of the plurality of measurement electrodes, a corresponding difference of potential between the reference electrode and a corresponding measurement electrode is determined. For each of the plurality of measurement electrodes, a corresponding voltage at a corresponding area of contact between the corresponding measurement electrode and the concrete structure is determined based on the reference voltage and on the corresponding difference of potential. For each of the plurality of measurement electrodes, a corresponding corrosion probability at the corresponding area of contact is determined based on the corresponding voltage at the corresponding area of contact.

According to a third aspect of the present disclosure, there is provided a system for evaluating a condition of steel reinforcements in a concrete structure. The system comprises a reference electrode, a measurement electrode, a voltmeter and a processing unit. The reference electrode is positionable on a first area on the concrete structure. The reference electrode comprises an electromagnetic sound unit. The measurement electrode is positionable on a second area of the concrete structure. The voltmeter is operatively connected to the reference electrode and to the measurement electrode and is adapted to determine a difference of potential between the reference electrode and the measurement electrode. The processing unit is operatively connected to the reference electrode and to the voltmeter. The processing unit is adapted to: perform an electromagnetic survey of the first area based on measurements from the electromagnetic sound unit, estimate a reference voltage for the reference electrode based on the electromagnetic survey, determine a voltage at the measurement electrode based on the reference voltage and on the difference of potential, and determine a corrosion probability at the second area based on the voltage at the measurement electrode.

According to a fourth aspect of the present disclosure, there is provided an electrode for performing an electromagnetic survey on a concrete structure. The electrode comprises a first wheel including an electromagnetic sound unit, and a second wheel mounted for rotating with the first wheel, the second wheel including a half-cell electrode placeable in electrolytic contact with a surface of the concrete structure.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which:

FIG. 7a is a chart that illustrates the result of a half-potential survey on reinforced concrete slab;

FIG. 7b is a chart that illustrates attenuation of EM waves in the same reinforced concrete slab as in FIG. 7a;

FIG. 11b is a schematic side view of the measuring wheel of FIG. 11a;

FIG. 12 is a flowchart of a first method for evaluating a condition of steel reinforcements in concrete;

Like numerals represent like features on the various drawings.

DETAILED DESCRIPTION

Figure 1:
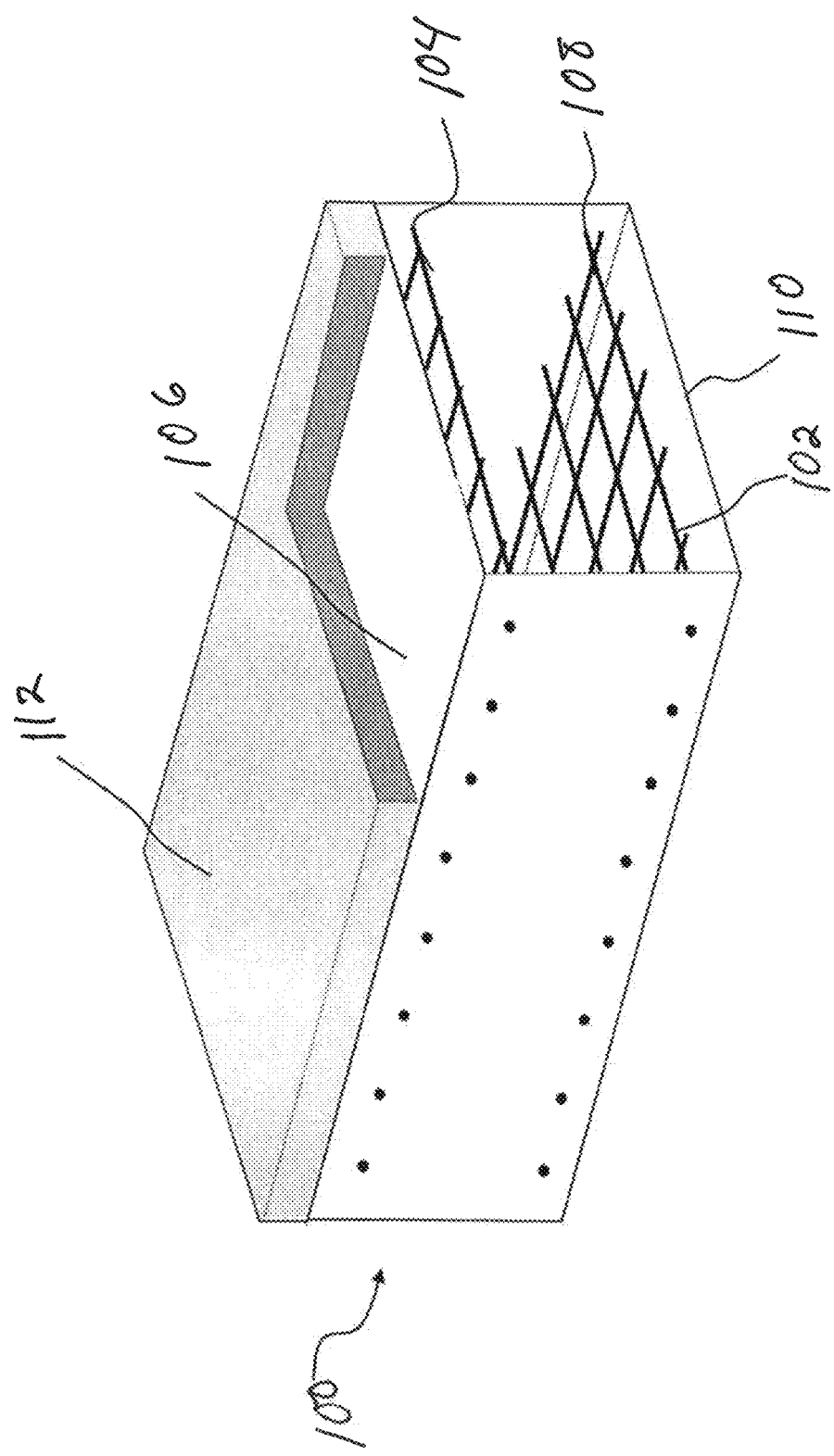
FIG. 1 is a schematic view of the composition of a typical reinforced concrete slab.

Various aspects of the present disclosure generally address one or more of the problems of determining the state of corrosion activity of steel reinforcement in reinforced concrete.

The present disclosure provides an improved corrosion potential method for obtaining information on the corrosion probability of steel reinforcements in a reinforced concrete element such as concrete bridge decks and slab floor of parking garages. This method does not have the disadvantages of the half-cell potential technique (ASTM C876). Some embodiments of this method are non-destructive. The method is applicable to most types of steel reinforcements in concrete.

The present disclosure also provides improved method for detecting and automatically indicating the probability of corrosion of steel reinforcement in concrete beneath the surface of a reinforced concrete element such as reinforced concrete bridge decks and slab floor of parking garages.

The present disclosure teaches to automatically record the position where the corrosion probability of steel reinforcement is high along a path of travel along a surface of a reinforced concrete element such as reinforced concrete bridge decks and slab floor of parking garages.

A method and apparatus are provided to determine the probability of corrosion of steel reinforcement in a reinforced concrete element without having appreciable influence of the reinforcement response neither the concrete cover thickness. This method and apparatus may be effective even if concrete surface is covered with an asphalt layer and/or a sealer, a coating as well as a waterproofing membrane of low electrical resistance.

An improved electrical potential method is also provided for the evaluation of the probability of corrosion of steel reinforcement in a reinforced concrete element in a mobile manner while traversing the surface of the element.

The present disclosure teaches to determine the corrosion probability of steel in reinforced concrete element having an asphalt overlay. Some embodiments of the present technology allow to determine the corrosion probability without the need to perforate this overlay to establish the electrical contact between the reference electrode and concrete surface The present disclosure further teaches to determine the corrosion probability of steel in reinforced concrete elements without being constrained to carry out a coring in the element to establish the electrical contact between rebar in concrete and a measuring device (voltmeter)

The present disclosure also teaches to determine the corrosion probability of steel reinforcement in reinforced concrete elements even if there is no electrical continuity between the steel reinforcements Most of the reinforced concrete elements such as reinforced concrete slabs contain two reinforcing grids, including one located near the top and the other located near the bottom. The Half-cell potential method allows only the evaluation of corrosion probability of the upper reinforcing rebar. The present disclosure provides a method and apparatus to determine the corrosion probability of steel reinforcements located near a top surface of reinforced concrete elements as well as steel reinforcements located near a bottom surface of reinforced concrete elements.

The present disclosure also provides an improved corrosion potential method for obtaining information on the corrosion probability of steel reinforcement in a reinforced concrete element according similar criteria's to those cited in the ASTM C876. Hence, it may be possible to compare the result obtained with the present disclosure with the results of surveys obtained several years ago with the ASTM C876 procedure on the same structure so the evolution of the corrosion activity may be evaluated.

The present disclosure is intended to help engineers to determine what part of a reinforced concrete element to be repaired, what kind of repair (surface repair or full thickness repair) and to correctly estimate the cost of such works The present technology involves measuring the electrical potential difference between at least two half-cell electrodes placed at a certain distance from each other, for example on the surface of the reinforced concrete element. One of these electrodes is a reference electrode. The potential of this reference electrode is estimated by measuring electromagnetic wave propagation characteristics in the concrete element at the reference electrode location. The electrical potential of the other electrodes is then determined. This makes it possible to determine the corrosion probability of rebars at the location of each half-cell electrode.

Unless otherwise specified, the term reinforced concrete slab in the following refers to reinforced concrete bridge decks, reinforced concrete floors of parking garages or any other reinforced concrete structural slab with or without asphalt overlay and/or sealer, coating or waterproofing membrane of low electrical resistivity.

Referring now to the Drawings, FIG. 1 is a schematic view of the composition of a typical reinforced concrete slab. Shown in FIG. 1 is a schematic view of a typical reinforced concrete slab 100 having a thickness of about 180 mm and contain reinforcements in the form of steel reinforcing rebars 102. The reinforced concrete slabs 100 contain two grids of reinforcing rebars 102 arranged at different depths. An upper reinforcing grid 104 is at about 40 mm from a top surface 106 of the slab 100 and a lower reinforcing grid 108 is at about 30 mm from a bottom surface 110 of the slab 100. In typical fashion, the diameter of rebars 102 is 16 mm and their spacing is about 150 mm. The reinforced concrete slab 100 is covered by an asphalt overlay 112 of a thickness of about 60 mm. The role of the asphalt overlay 112 is to protect the reinforced concrete slab 100 against the infiltration of chloride ions. Although FIG. 1 and later Figures describe the present technology by reference to rebars 102 in a concrete slab 100, the present technology is equally applicable to other concrete structures that may include other types of steel reinforcements, for example cables or anchors. Mentions of rebars 102 in a concrete slab 100 are for illustration purposes and are not intended to limit the present disclosure.

Figure 2:
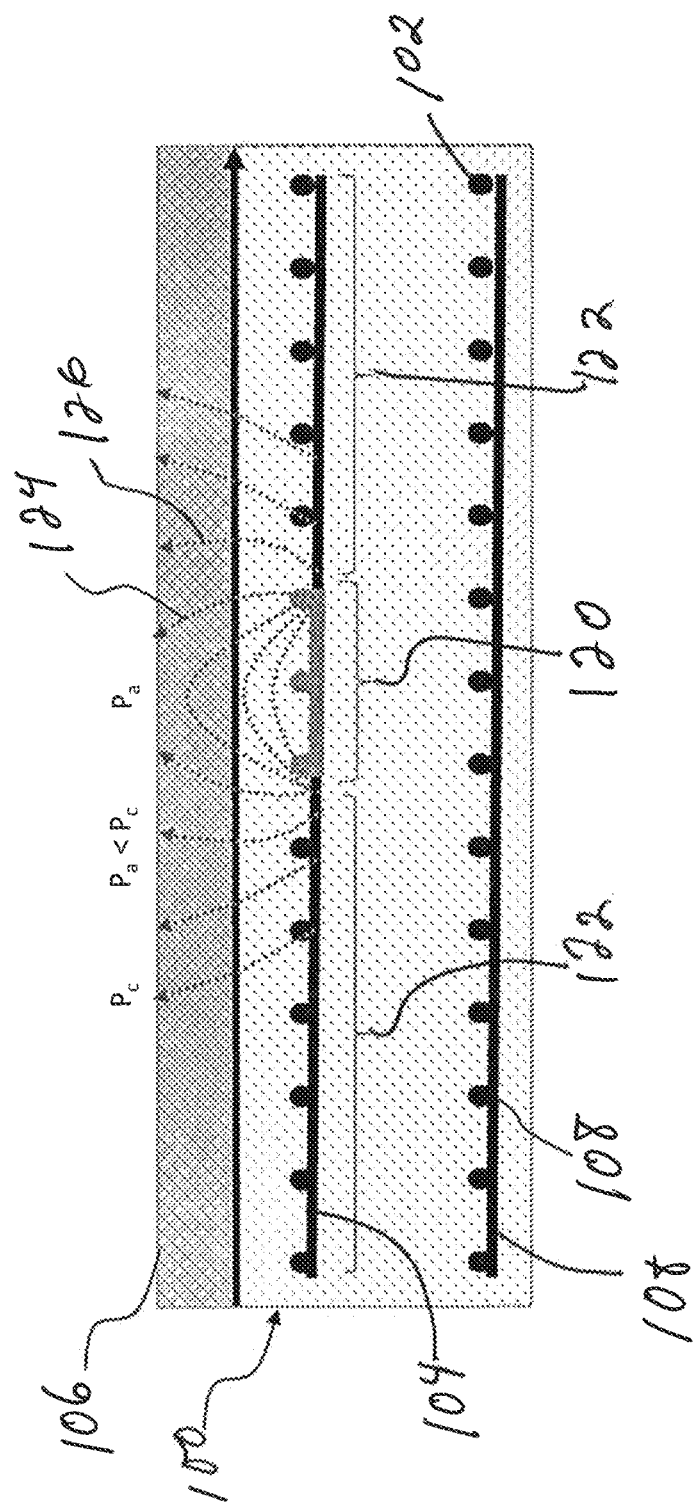
FIG. 2 is a schematic view that illustrates rebar corrosion in a reinforced concrete slab.

As mentioned above, corrosion of reinforcement in concrete is generally induced by the infiltration of chloride ions dissolved in water through the pores and micro-cracks in the asphalt overlay 112 and in the concrete. Referring now to FIG. 2, an area contaminated by chloride ions becomes an anode location 120 with the remaining area becoming cathode locations 122. At the anode location 120, iron atoms lose electrons and that migrate into the surrounding concrete as ferrous ions. The released electrons flow through rebars 124 in cathode locations 122 where they combine with oxygen and water in the concrete to form hydroxyl ions. Ferrous ions migrate to the cathode locations 122 where they combine with the hydroxyl ions. Current flow due to ions migration through the concrete between anodic locations 120 and cathodic locations 122 is accompanied by an electric potential field 126 surrounding the rebars 124 that are subject to corrosion. As shown in FIG. 2, equipotential lines intersect the top surface 106 of the slab 100. In an area above the anode location 120, the potential has a value $P_a$ and, some distance away at the cathode location 122, the potential has a value $P_c$. The value of $P_a$ is normally lower than that of $P_c$ so local corrosion areas above the anode location 120 can be identified by mapping equipotential contours on the top surface 106.

Figure 3:
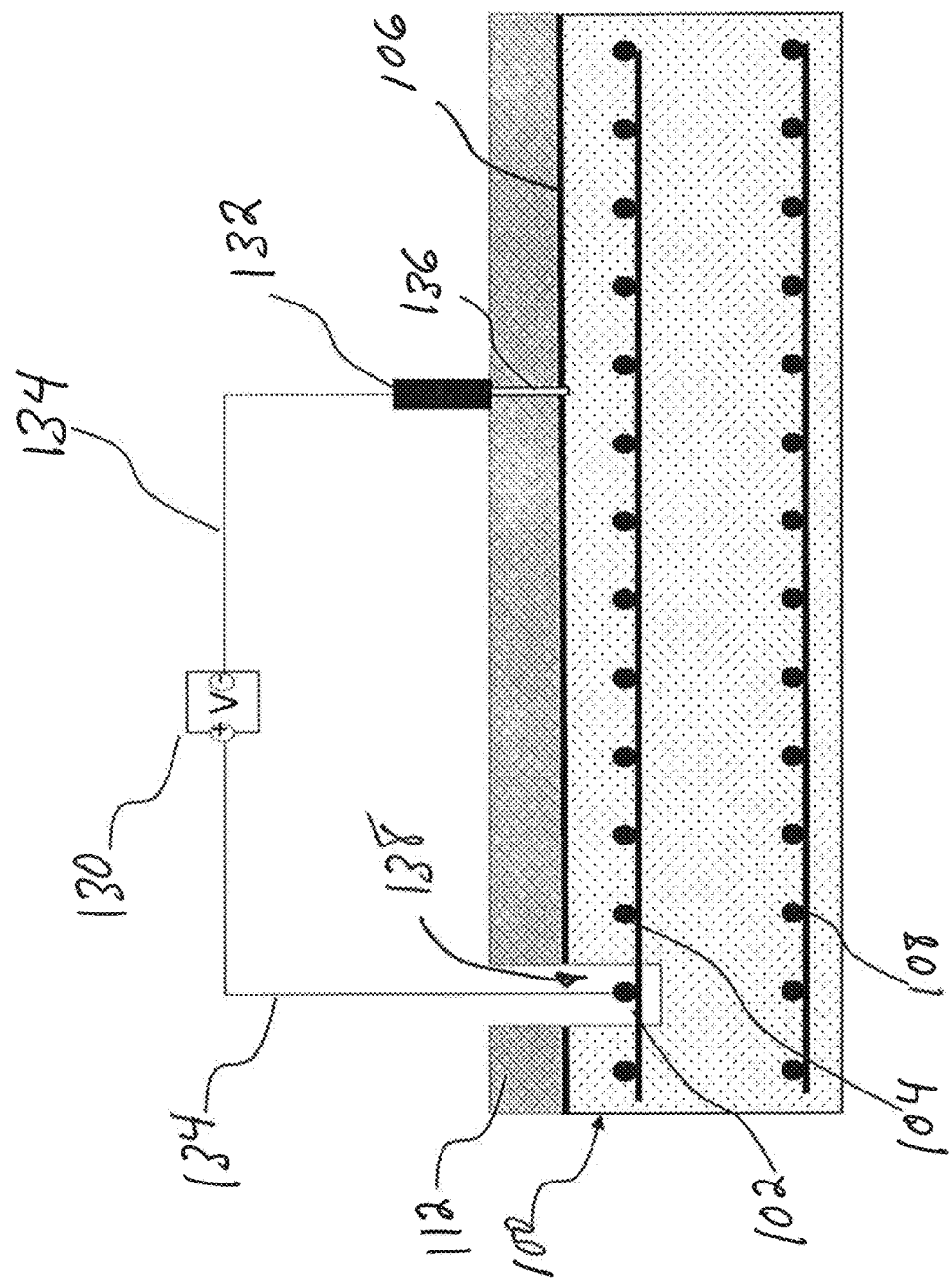
FIG. 3 is an illustration of the principle of the half-cell potential technique.

Half-cell potential is the most used technique to detect corrosion activity of rebars 102 in reinforced concrete slabs 100. FIG. 3 summarily explains its principle which is described in detail in the ASTM C876—*Standard Test Method for Corrosion Potentials of Uncoated Reinforcing Steel in Concrete*. FIG. 3 shows a cross-section of a reinforced concrete slab 100 with an upper reinforcing grid 104 and a lower reinforcing grid 108. This reinforced concrete slab 100 has an asphalt overlay 112. The Half-cell potential measurement consists in measuring the potential difference with a voltmeter 130 between a portable reference electrode 132 (usually a copper-copper sulfate (CSE) electrode) in contact with the top surface 106 of the reinforced concrete slab 100 and with a given rebar 102 of the upper reinforcing grid 104 located below the concrete surface. The rebar 102 and the reference electrode 132 are connected to the voltmeter 130 by electrical cables 134. The contact between the reference electrode 132 and the top surface 106 of reinforced concrete slab 100 is achieved by drilling a hole 136 through the asphalt overlay 112 and filling it with a conductive solution. The electrical contact between the given rebar 102 and the voltmeter 130 is achieved by locating the given rebar 102 in the concrete slab 100 and exposing it by coring 138 through the asphalt overlay 112 and the top surface 106 of the concrete slab 100.

Generally, half-cell potential surveys are carried out on a regular interval grid of about 1 m by 1 m. Before starting a potential survey on the reinforced concrete slab 100, the electrical continuity of the reinforcing steel rebars 102 in the concrete slab 100 needs to be established. This is performed by exposing some rebars 102 in two opposite sides of the slab 100 and measuring electrical resistivity between them. This resistance should be in the order of 1 Ohm. Once this electrical continuity is verified, the voltmeter is connected to one of these rebars 102, and the potential measurements are done by moving the reference electrode 132 on many points of the interval grid.

This conventional technique requires making electrical contact between the rebars 102 and the voltmeter 130 and between the half-cell electrode 132 and the top surface 106 of the slab 100, in many cases requiring drilling through asphalt overlay 112. Rebars 102 need to be exposed at two areas to establish electrical continuity of the rebars 102. This destructive testing technique is time intensive and needs to be followed by expensive repairs. Although some embodiments of the present technology may be used with such drilling operations, other embodiments may avoid the need for drilling through the asphalt overlay 112.

When a steel rebar 102 is corroding, the excess of electrons in the rebar 102 tends to flow from the rebar 102 to the half-cell electrode 132. The positive terminal of the voltmeter 130 being connected to the rebar 102, the voltmeter 130 indicates a negative voltage. An important negative voltage reading is interpreted to mean that the rebar 102 has a large excess of electrons, indicative of a high corrosion probability. Table I shows potential values that are generally accepted as revealing active and passive conditions of a rebar 120:

TABLE I

| Half-Cell potential reading (mV) vs. Cu/CuSO$_4$ | Corrosion activity |
| --- | --- |
| Greater than −200 mV | Corrosion probability less than 10% |
| Between −200 mV and −350 mV | 50% Corrosion probability |
| Lower than −350 mV | Corrosion probability greater than 90% |

Figure 8:
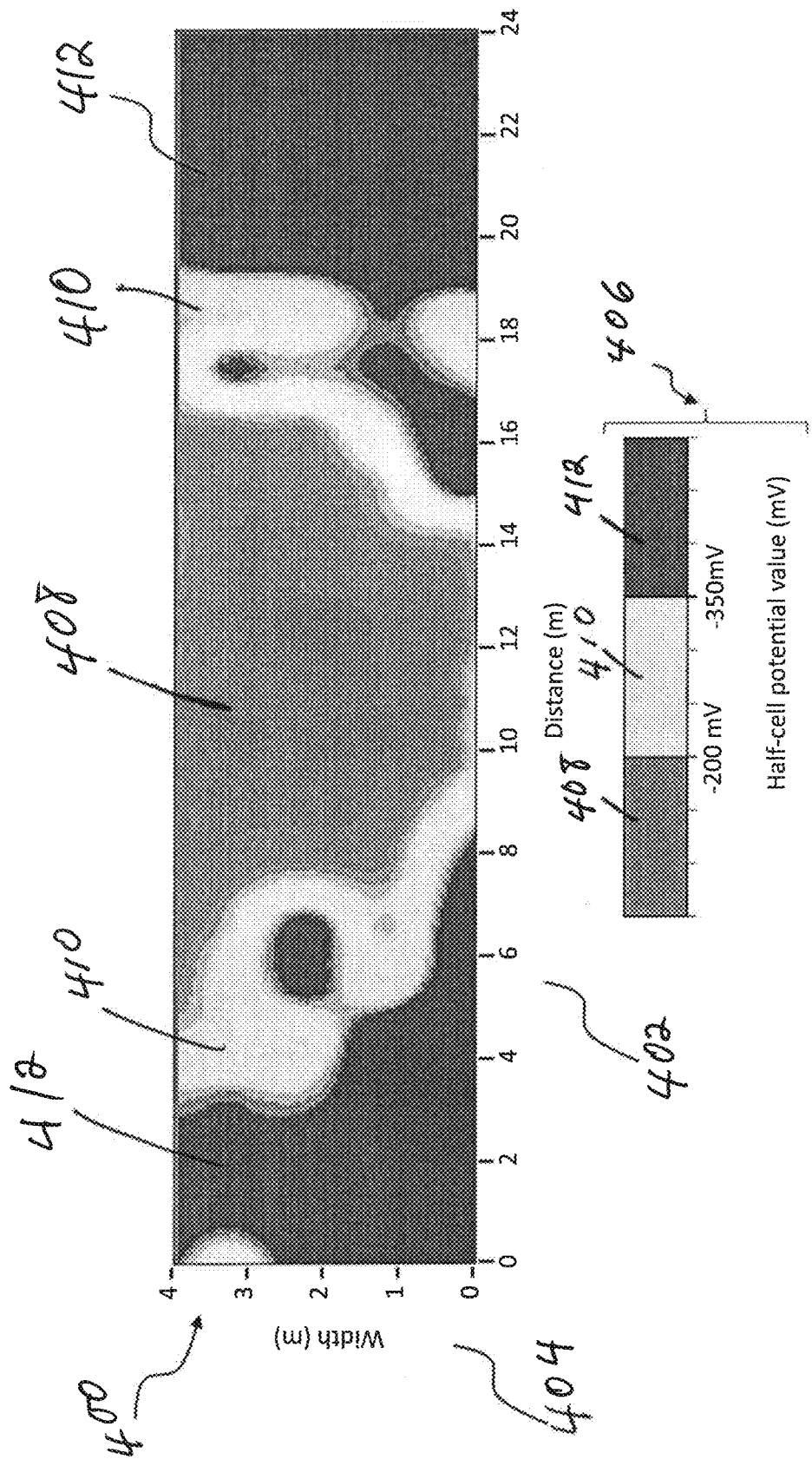
FIG. 8 shows a result of a half-potential survey conducted on a reinforced concrete slab and presented as a contour map.

FIG. 8 (described later) will show that a result of a potential survey is generally presented in the form of a contour map that indicates areas where the corrosion probability of rebars in the reinforced concrete slab in high, based on half-cell potential readings.

Figure 4:
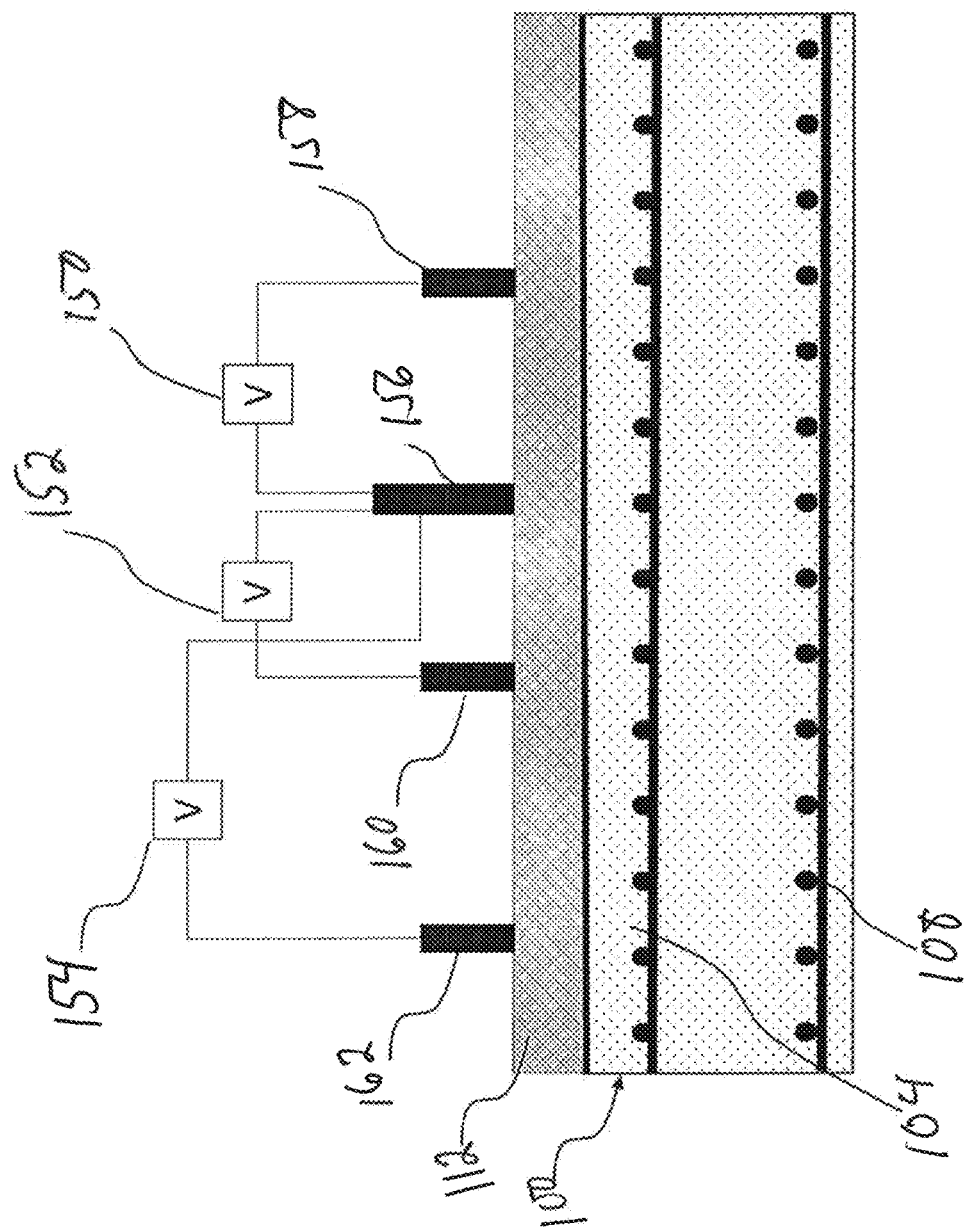
FIG. 4 is a schematic representation of a potential measurement technique according to an embodiment of the present disclosure.

FIG. 4 explains a principle behind the present disclosure. This principle consists in measuring the difference U with voltmeters 150, 152 and 154 of electrical potential between a reference (Re) half-cell electrode 156 and one or several other measuring half-cell electrodes 158, 160 and 162 placed at a selected distance from each other. In the example of FIG. 4, the half-cell electrodes 158, 160 and 162 are positioned on the surface of the asphalt overlay 112, or directly at the surface of the concrete slab 100 when the asphalt overlay 112 is not present. A potential difference U between a potential V(Re) of the reference electrode 156 and the potential V(i) of a given measuring electrode 158, 160, 162 is given by the equation: U=V(Re)−V(i). The potential difference U between the potential V(Re) of reference electrode and the potential V(i) of a given measuring electrode 158, 160, 162 is a relative measure and does not suffice to determine the corrosion probability of the rebars 102 at the location of these measuring electrode 158, 160, 162, in view of the criteria presented in Table I. However, knowledge of potential value V(i) of a given measuring electrode 158, 160, 162 located at a given position makes it possible to obtain a preliminary assessment of a corrosion probability of rebars 102 at this location. Determination of the potential values V(i) of the measuring electrodes 158, 160, 162 is further determined using knowledge of the potential value V(Re) of the reference electrode 156. It should be noted that this potential value of the reference electrode 156 may also be obtained using the drilling technique illustrated in FIG. 3.

In an embodiment of the present disclosure, the potential value V(Re) of the reference electrode (Re) 156 is estimated in a non-destructive and rapid manner from a measure of an electromagnetic (EM) wave propagation characteristics in the reinforced concrete slab 100 at the location of the reference electrode 106. The potential value of the reference electrode is generally lower than −350 mV if the EM wave attenuation is high, and it is generally higher than −200 mV if the EM wave propagation attenuation is low.

Electromagnetic sounding is a non-destructive testing civil engineering technique that uses EM wave propagation to assess the condition of reinforced concrete structures. The principle of this technique is summarily illustrated in FIG. 5. A transmitting antenna 170 transmits an EM wave into the interior of reinforced concrete slab 100, and a receiving antenna 172 receives various reflections of this wave coming from the interior of the reinforced concrete slab 100. Reflections 174 come from the top surface 106 of the concrete slab 100. Reflections 176 come from rebars 102 in the upper reinforcing grid 104. Reflections 178 come from rebars in the lower reinforcing grid 108. Reflections 180 come from the bottom surface 110 of the concrete slab 100. By moving the antennas 170 and 172 along the slab 100 in the direction shown by arrow 182 while continuously transmitting EM waves into the concrete slab 100 and receiving the reflections 174, 176, 178 and 180, it is possible to obtain a 2-dimensional image indicating the reflections of the EM wave that occur within the reinforced slab 100. A computer 184 coupled to the antennas 170 and 172 manages a data acquisition process as well as real time visualisation of the data on a screen (not shown).

Figure 5:
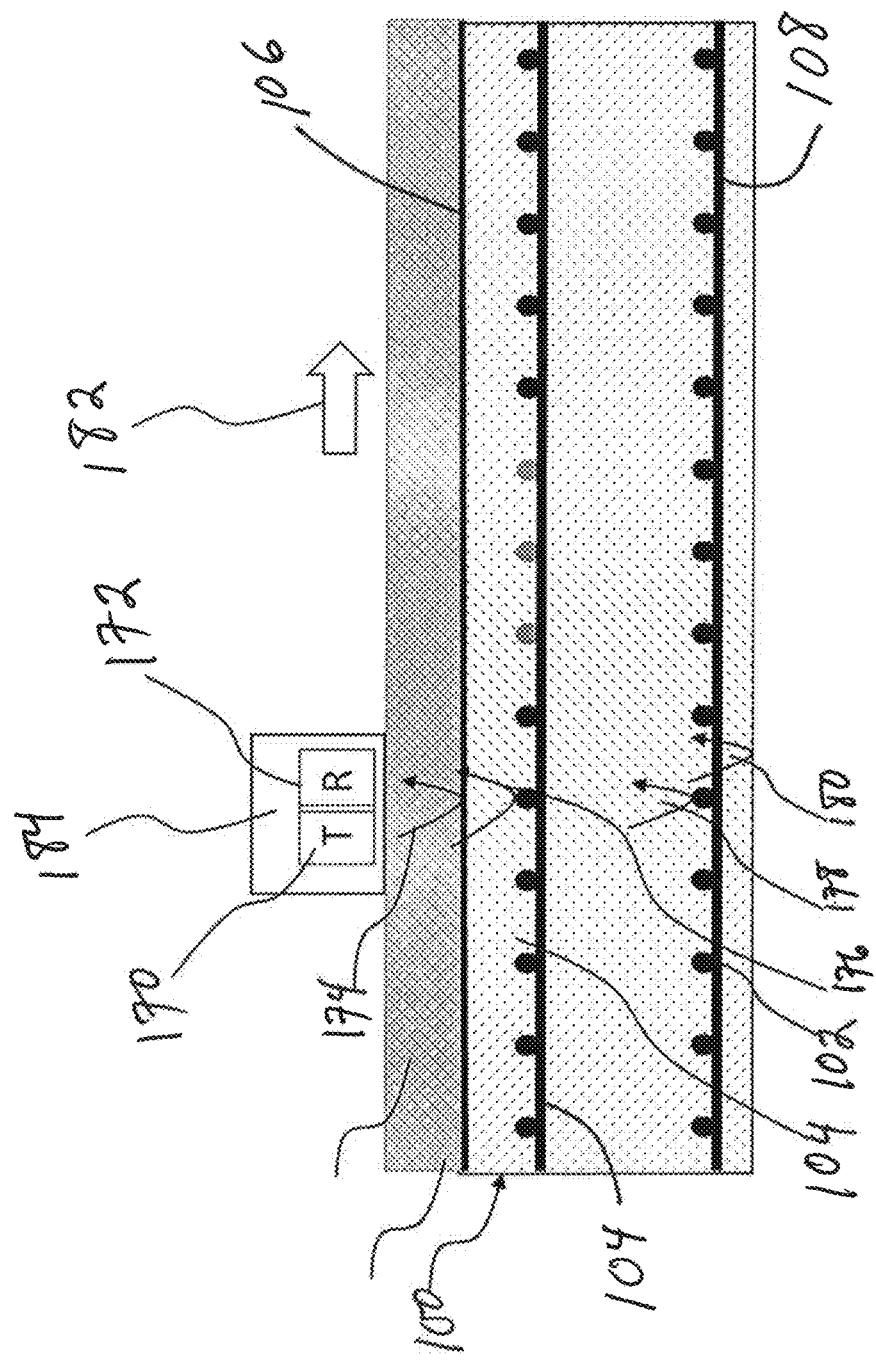
FIG. 5 is a schematic representation of a principle of the EM sounding technique.
Figure 6:
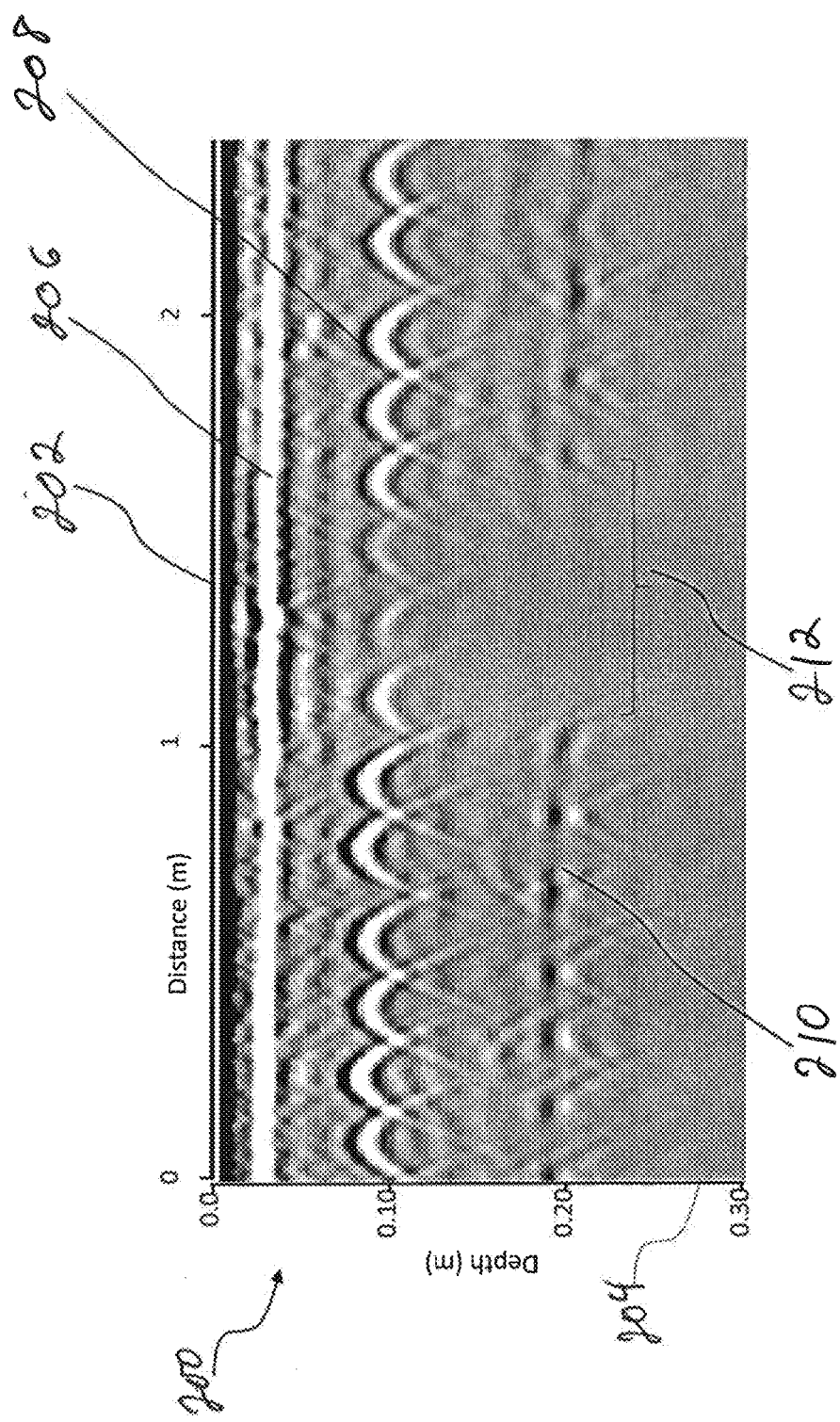
FIG. 6 is a an example of a EM sounding image.

FIG. 6 shows a typical 2-dimensional electromagnetic (EM) sounding image 200 that was obtained during an EM survey on a reinforced concrete slab 100 with an asphalt overlay 112 similar to that shown in FIG. 5. A horizontal axis 202 represents a distance along the surface 106 of the slab 100 while a vertical axis 204 represents a depth in the slab 100. Reflections of the EM waves are visible as follows: Reflections 206 are from the surface 106 of the slab 100, reflections 208 (hyperbolas) are from the rebars 102 of the upper reinforcing grid 104, and reflections 210 are from the bottom surface 110 of the slab 100. Reflections from the rebars 102 of the lower reinforcing grid 108 are generally hidden by the reflections 208 and are not visible in the image. FIG. 6 shows that the reflection intensity of EM wave from the rebars 102 to the upper reinforcing grid 104 as well as the reflection intensity from the bottom surface 110 of the concrete slab 100 is attenuated in an area 212. This attenuation of EM wave is caused by a high electrical conductivity of the concrete in this area 212, this high electrical conductivity being due to a high chloride ions content in the concrete in this area 212. Therefore, the corrosion probability of rebars 102 in this area 212 is high, and it is expected that a half-cell potential survey would show a value lower than −350 mV in this area 212.

Figures 7A, 7B:
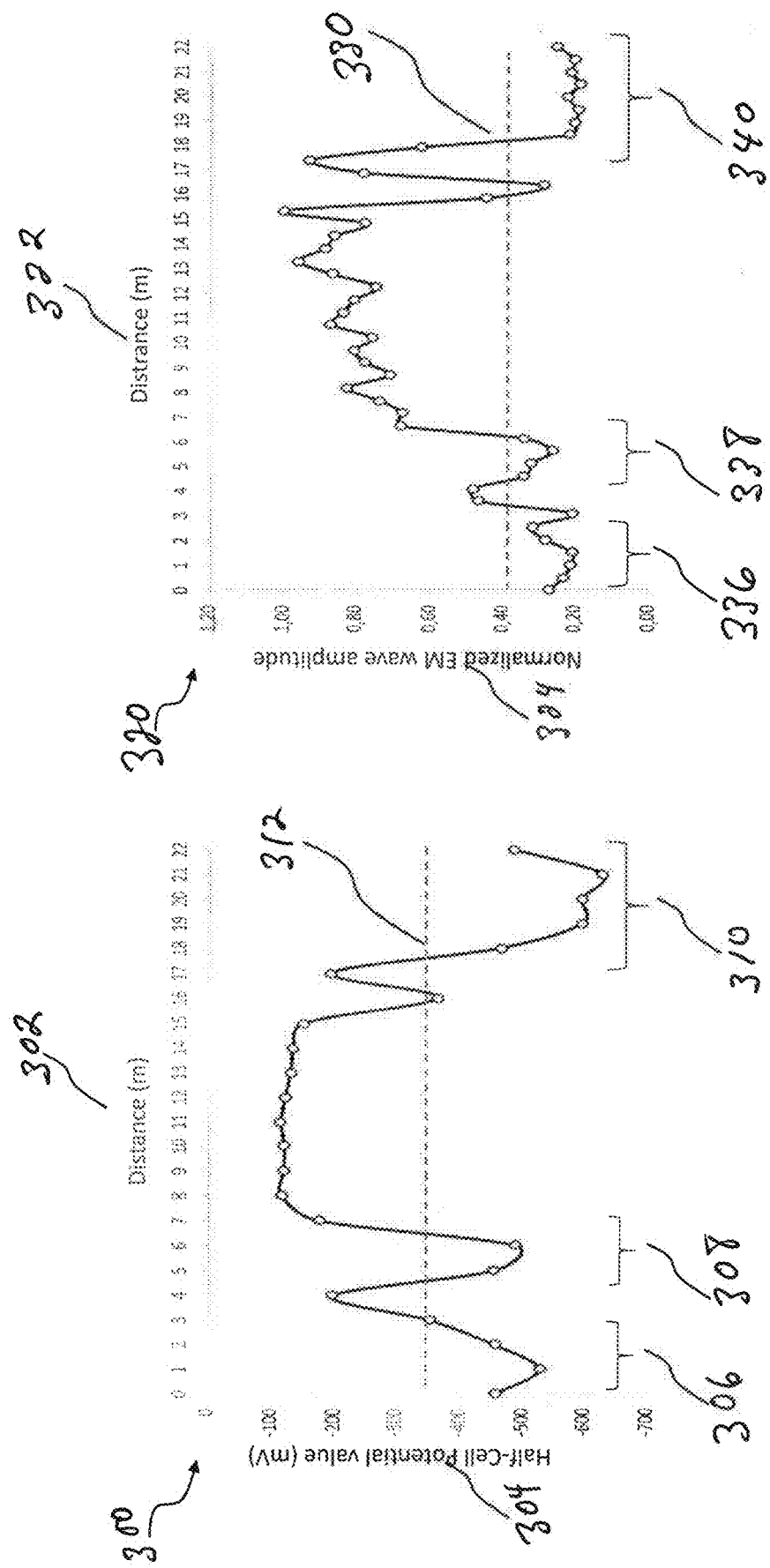

FIG. 7a is a graph 300 showing a result of a half-cell potential survey performed according to the specifications of the ASTM C876. This survey was done along a line of 22 m length at the surface of a reinforced concrete slab with an asphalt overlay. In FIG. 7a, a horizontal axis 302 is a distance along the concrete slab and a vertical axis 304 is a measured half-cell potential value. The result indicates that in some areas 306, 308 and 310, the half-cell potential value is lower to a value 312 (−350 mV) below which the corrosion probability of rebars is high.

FIG. 7b is a graph 320 showing a result of an EM sounding survey conducted along the same line of the reinforced concrete slab that was used to produce the results shown on FIG. 7a. A horizontal axis 322 is the distance and corresponds to the horizontal axis 302 of FIG. 7a. A vertical axis 323 is a normalized amplitude of EM wave reflection in the slab. Referring again to FIG. 6, this result is achieved by first submitting collected reflection data to a basic signal processing device (not shown). A running average of the EM sounding image is performed over a given distance along the horizontal axis 202. A sum amplitude along depth of the slab 100 on the vertical axis 204 of the image is then calculated at each location along the horizontal axis. Using a threshold amplitude 330 set to about 0.40, which is a dimensionless value, FIG. 7b indicates that attenuation of EM wave is high in areas 336, 338 and 340, corresponding respectively to areas 306, 308 and 310 of FIG. 7a. Hence, areas where EM wave attenuation is high coincide with areas where half-cell potential value is lower than −350 mV. On the other hand, areas where attenuation of EM wave is low coincide with areas where half-cell potential value is higher than −200 mV FIG. 8 shows a result of a half-cell potential survey conducted on a reinforced concrete slab according the specification of the ASTM C876. This slab has and an asphalt overlay. Its length 402 is 24 meters and its width 404 is four (4) meters. On FIG. 8, a chart 406 reproduces the potential values of Table I, in which areas 408 reflect a low corrosion probability (less than 10%, voltage reading greater than −200 mV), areas 410 reflect a medium corrosion probability (50%, voltage reading between −200 and −350 mV), and areas 412 reflect a high corrosion probability (greater than 90%, voltage reading lower than −350 mV). The same reference numbers 408, 410 and 412 are reproduced in corresponding low, medium and high corrosion probability areas on a contour map 400.

Figure 9:
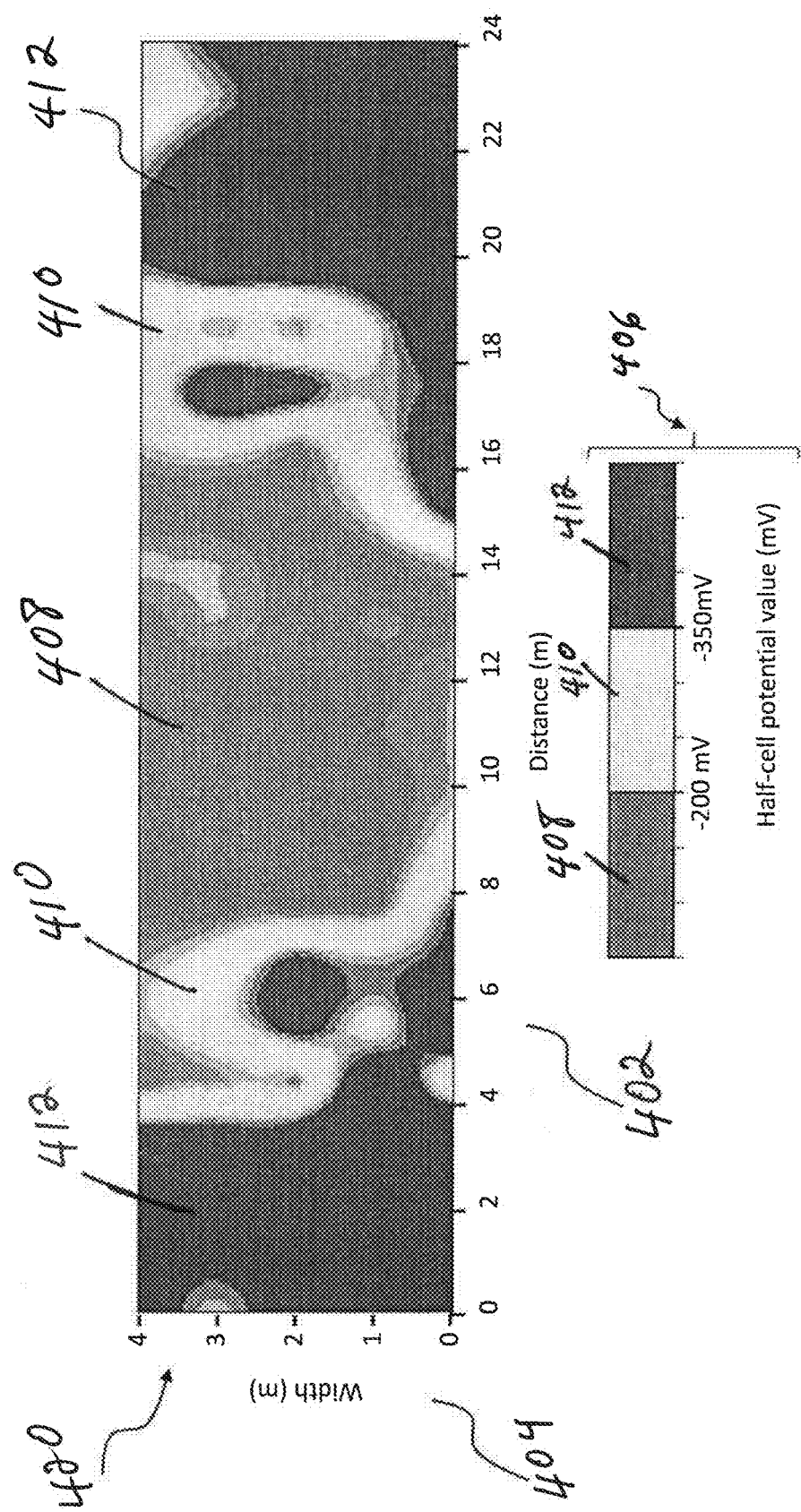
FIG. 9 shows a result of a potential survey conducted on a reinforced concrete slab according some of the embodiments of the present disclosure and presented as a contour map.

FIG. 9 shows a result of a survey conducted according some of the embodiments of the present disclosure on the same reinforced concrete slab described in FIG. 8. On FIG. 9, a contour map 420 shows the same dimensions 402 and 404 as shown on FIG. 8. The same chart 406 is also provided for comparison purposes. The contour map 420 indicates the areas where the corrosion probability of rebars in the reinforced concrete slab is high (areas 412), medium (areas 410) or low (area 408). Comparison of FIG. 9 to FIG. 8 shows clearly that the result obtained by the present disclosure is similar to the one obtained by the traditional method as described in ASTM C876.

Figure 10:
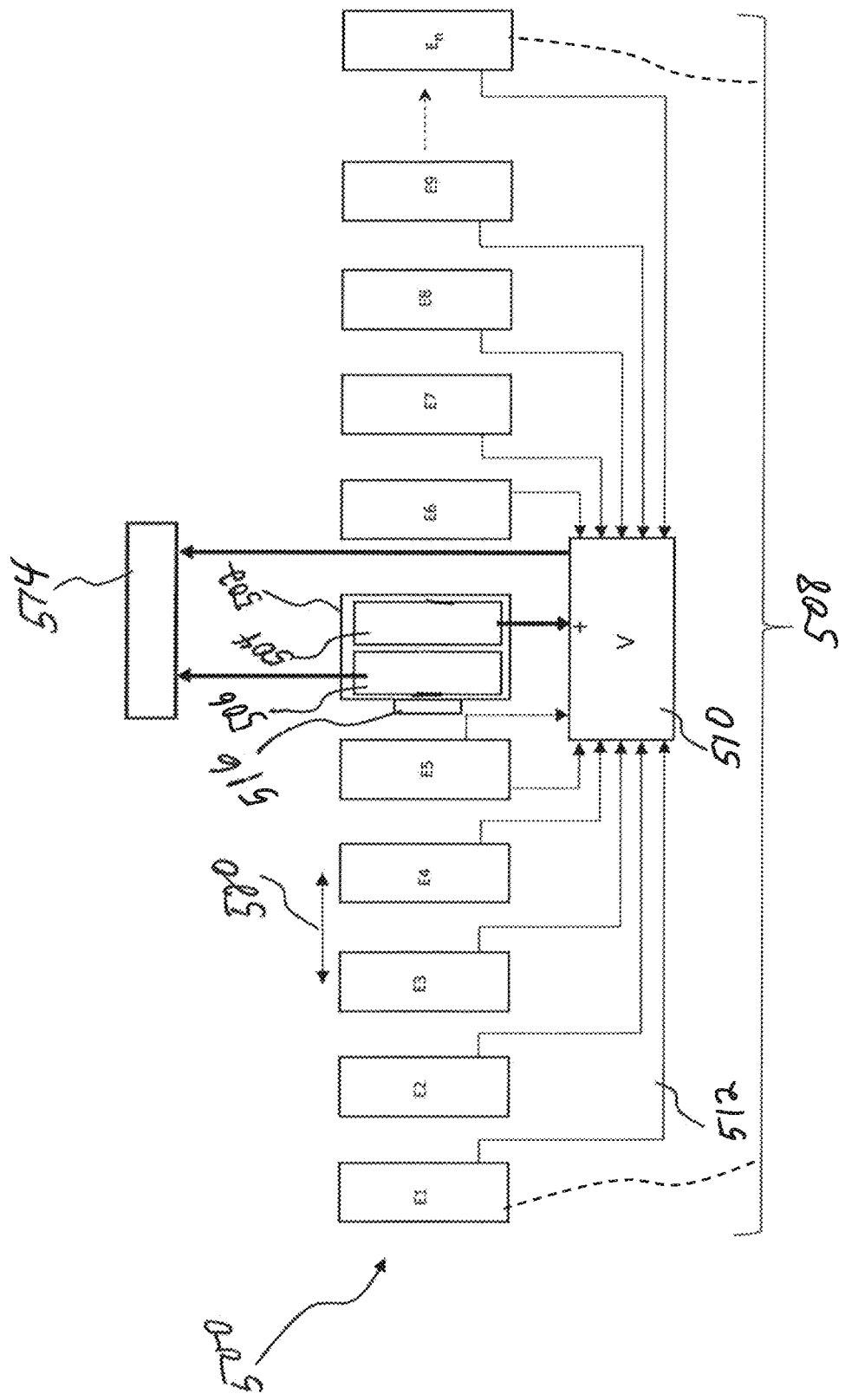
FIG. 10 is a schematic representation of an inspection system according to some embodiments of the present disclosure.

FIG. 10 is a schematic representation of an inspection system according to some embodiments of the present disclosure. This system 500 includes at least one reference electrode mounted in a rollable support, for example a reference wheel 502, which is divided in two parts: a part containing a half-cell potential reference electrode 504, and another part containing various components of an EM sound unit 506 used for the EM sounding of the reinforced concrete slab 100. The inspection system 500 also contains a group 508 of one or several secondary movable electrodes mounted on respective rollable supports, for example secondary wheel electrodes E1-En. The secondary wheel electrodes E1-En are typical, commercially available electrodes. The inspection system 500 further comprises a high impedance voltmeter 510 and electrical cables 512 that connect the electrodes E1-En to the voltmeter 510. The wheel electrodes E1-En may be linearly aligned or not. The reference electrode 504 and the wheel electrodes E1-En share comparable characteristics, being for example cooper-cooper sulfate electrodes or any other suitable electrodes for this application. Each electrode 504 and E1-En is equipped with a reservoir containing a conductive solution (not shown), which makes it possible to moisten the surface of the asphalt overlay 112 or the surface of the concrete slab 100 at a measurement point for the electrode to provide electrolytic contact between the surface and the electrode. Distances between the reference electrode 504 and each one of electrodes E1-En as well as the number of the electrodes E1-En and a distance 520 between each of the electrodes E1-En are variable and may be fixed by an operator of the inspection system 500 and stored in a processing unit 514, depending for example on a surface area to be investigated and/or on a desired measuring density. The voltmeter 510 measures potential differences between the reference electrode 504 and each of the secondary electrodes E1-En. The results of these measurements are transmitted to the processing unit 514. At the same time, the data collected by the EM sounding unit 506 is also transmitted to the processing unit 514. The processing unit 514 computes EM wave propagation characteristics at the measurement location of the reference electrode 504 and estimates the potential of the reference half-cell potential at that location. The processing unit 514 receives potential differences between the reference electrode 504 and the secondary electrodes E1-En and determines the potential of each secondary electrode E1-En. Measurement information is saved in a memory unit (not shown) of the central processing unit. The processing unit 514 determines the variation of the electrical potential at the surface of the structure under investigation and display the result on a screen (not shown) in the form of a contour map or any other relevant format. The entire inspection system 500, including in particular the electrodes 504 and E1-En, may be designed to be automatically or manually movable on the surface of the concrete slab to be investigated or pulled by a vehicle. A measuring wheel 516 may be coupled to the reference electrode 504 and roll with the rotation of the reference wheel 502 on the surface. The processing unit 514 may use distance and/or location information from the measuring wheel 516 to trigger and stop the data acquisition and to locate the position of the reference electrode 504 on the surface of the concrete.

Figure 11B:
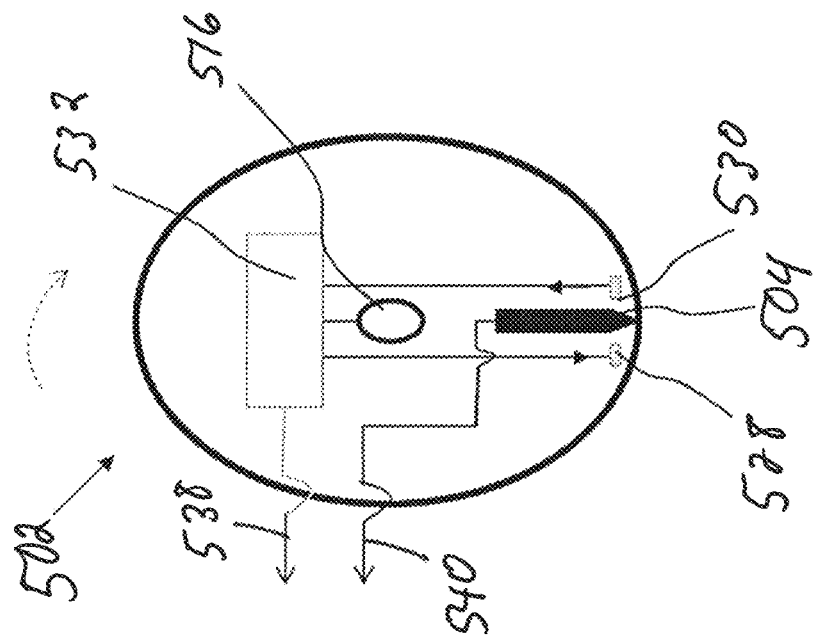
Figure 11A:
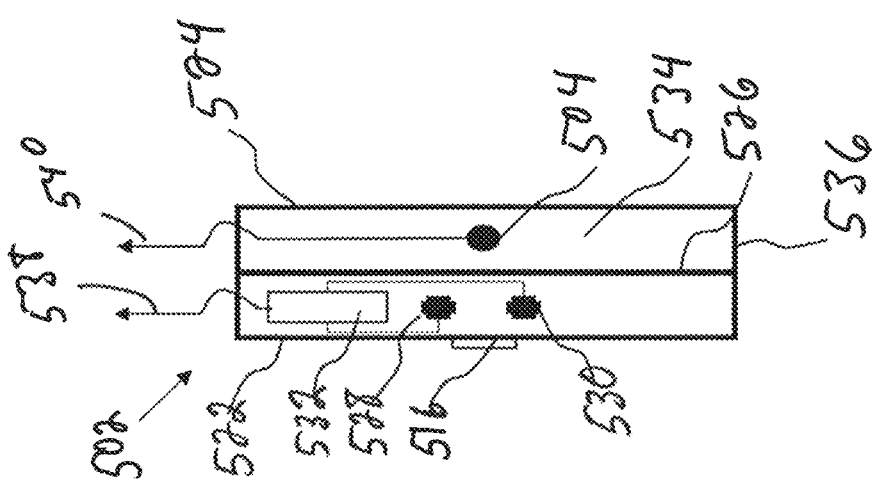
FIG. 11a is a schematic top view of a measuring wheel according to an embodiment.

FIG. 11a is a schematic top view of a measuring wheel according to an embodiment. FIG. 11b is a schematic side view of the measuring wheel of FIG. 11a. Referring at once to FIGS. 10, 11a and 11b, an embodiment of the reference wheel 502 comprises two wheels 522 and 524 separated by a watertight bulkhead 526. The wheel 524 contains the half-cell reference electrode 504. The wheel 522 contains components of the EM sound unit 506, including a transmitting antenna 528 and a receiving antenna 530, the antennas 528 and 530 being arranged in the reference wheel 502 so as to remain oriented towards and close to the asphalt or concrete surface as the reference wheel 502 moves along the surface. In a non-limiting embodiment the antennas 528 and 530 have a center frequency of 2 GHz. Use of other antenna types and use of other frequencies is also contemplated. Transmission of EM wave into the concrete slab 100 and detection of reflections of these waves are controlled by a control unit 532 containing hardware and software components, for example a processor and a memory (not shown). The wheel 522 may be made of plastic or any other material that does not significantly affect the transmission of EM wave in the concrete and the reception of their reflections. The wheel 524 includes a reservoir 534 containing a conductive solution. A surface 536 of this wheel 524 that comes in contact with the surface may be in any suitable material that allows electrolytic contact, using the conductive solution, between the reference electrode 504 and the surface. The measuring wheel 516 allows to trigger and to stop the data acquisition as well as the localization of the measurement along the surface. Signalling links 538 and 540 respectively connect the control unit 532 and the reference electrode 504 to the processing unit 514.

FIG. 12 is a flowchart of a first method for evaluating a condition of steel reinforcements in concrete. A sequence 600 includes a plurality of operations, some of which may be executed in different orders, some of which are optional. The operations are as follows:

Operation 604: A reference electrode is positioned on a first area on the concrete structure 100, for example on a surface of the concrete structure 100 (or on the asphalt overlay 112, when present).

Operation 606: An electromagnetic survey is performed, using for example the EM sounding unit 506, in order to estimate a reference voltage V(Re) for the reference electrode. The reference voltage is set to a high value when the electromagnetic survey indicates a low corrosion probability. Table I suggests values of at least −200 mV or higher for this high value. A slightly higher value, for example about −150 mV, may be selected in order to account for measurement inaccuracies. In the same manner, the reference voltage is set to a low value when the electromagnetic survey indicates a high corrosion probability. Table I suggests values equal to or lower than −350 mV for this low value. A lower value, for example about −400 mV, may be selected in order to account for measurement inaccuracies.

Operation 608: A measurement electrode is positioned on a second area of the concrete structure.

Operation 610: A difference of potential U is determined between the reference electrode and the measurement electrode.

Operation 612: A voltage V(i) at the measurement electrode is determined based on the reference voltage and the difference of potential, for example by calculating V(i)=V(Re)−U.

Operation 614: A corrosion probability at the second area is determined based on the voltage V(i) at the measurement electrode. A high corrosion probability is determined at the second area if the reference voltage V(Re) has the low value and the voltage V(i) is less than a sum of the reference voltage V(Re) plus a first predetermined threshold, for example about 50 mV. A low corrosion probability is determined at the second area if the reference voltage V(Re) has the high value and the voltage V(i) is more than the reference voltage V(Re) minus a second predetermined threshold, for example about 50 mV. A high corrosion probability is determined at the second area if the reference voltage V(Re) has the high value and the voltage V(i) at the second area is lower than the reference voltage V(Re) by at least a third predetermined threshold, for example about 200 mV. A low corrosion probability is determined at the second area if the reference voltage V(Re) has the low value and the voltage V(i) at the second area is higher than the reference voltage V(Re) by at least a fourth predetermined threshold, for example about 200 mV.

Operation 616: The measurement electrode is repositioned to successive additional areas.

Operation 618: Successive differences of potential U are determined between the reference electrode and the measurement electrode at each of the successive additional areas.

Operation 620: Successive voltages V(i) at the measurement electrode are determined based on the reference voltage V(Re) and on the successive differences of potential U.

Operation 622: A corresponding corrosion probability is determined at each of the successive additional areas based on the successive corresponding voltages V(i) at the measurement electrode.

The person of ordinary skill in the art will readily appreciate that voltage measurements made on concrete structures as well as estimations of reference voltages based on electromagnetic surveys performed on concrete structures will provide values having significant tolerances. For that reason, the present disclosure provides approximate values for such measurements. Voltage measurements and estimations that the skilled reader would consider sufficiently close of the numerical values provided herein for proper operation of the present technology are considered part of the present disclosure.

Figure 13:
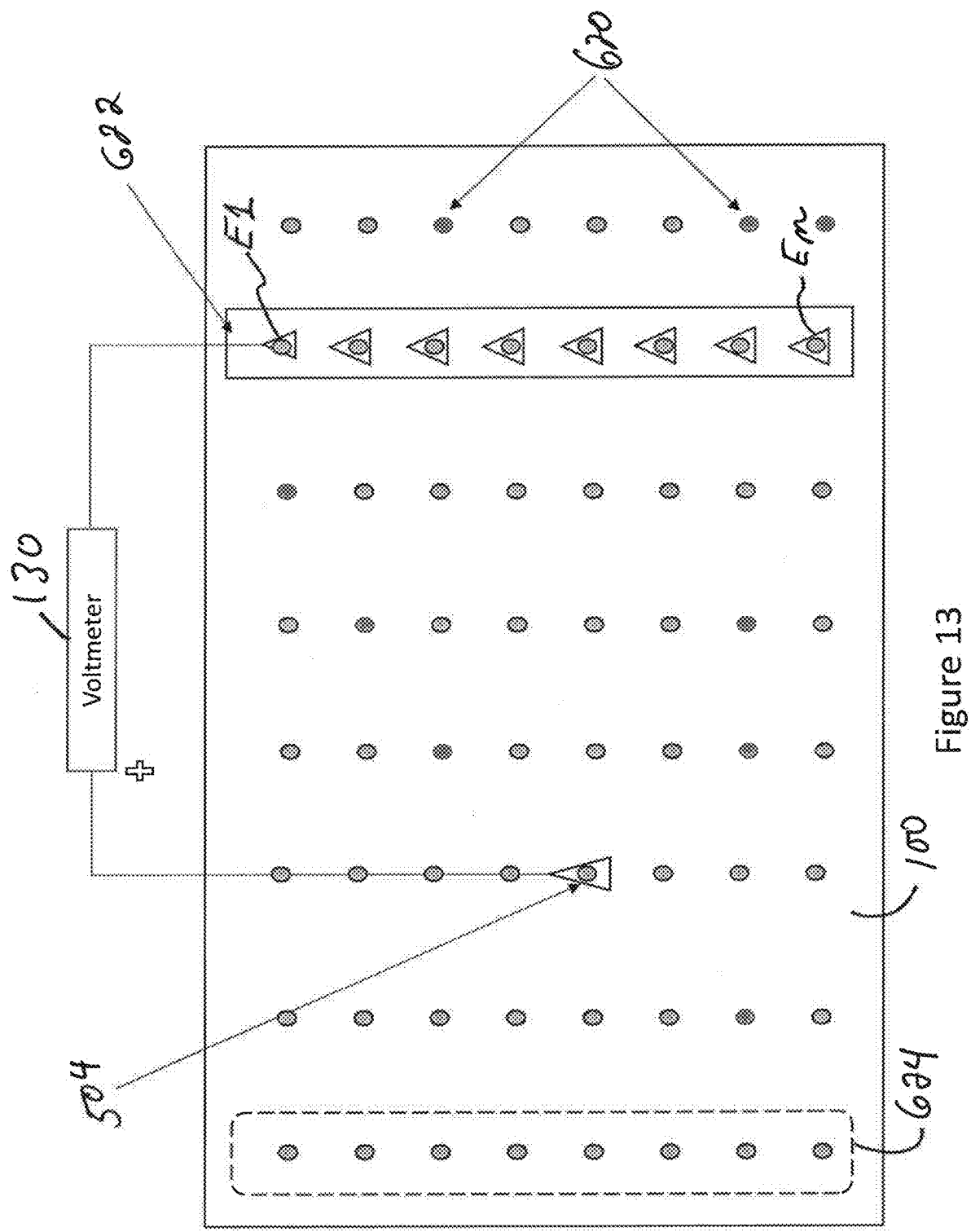
FIG. 13 is a top plan view of a concrete structure illustrating the method of 12.

A plurality of measurement electrodes may be used concurrently. FIG. 13 is a top plan view of a concrete structure illustrating the method of FIG. 12. In addition to the reference electrode 504, a plurality of additional measurement electrodes E1-En is positioned on a corresponding plurality of additional areas 620 of the concrete structure 100. The measurement electrode and the additional measurement electrodes (collectively E1-En) forming an electrode array 622, the second area and the additional areas forming an array (for example 624) of areas 622 on the concrete structure 100. The electrode array 622 is used to determine a corresponding voltage at each area 620 of the array of areas. A corresponding corrosion probability at each area 620 of the array of areas is determined based on a corresponding difference of potential between the reference voltage and the corresponding voltage. The electrode array 622 may be repositioned to successive additional arrays 624 of areas 620 where one of the E1-En is temporarily located, in view of determined a corrosion probability at each of the areas 620 of the concrete structure 100.

Figure 14:
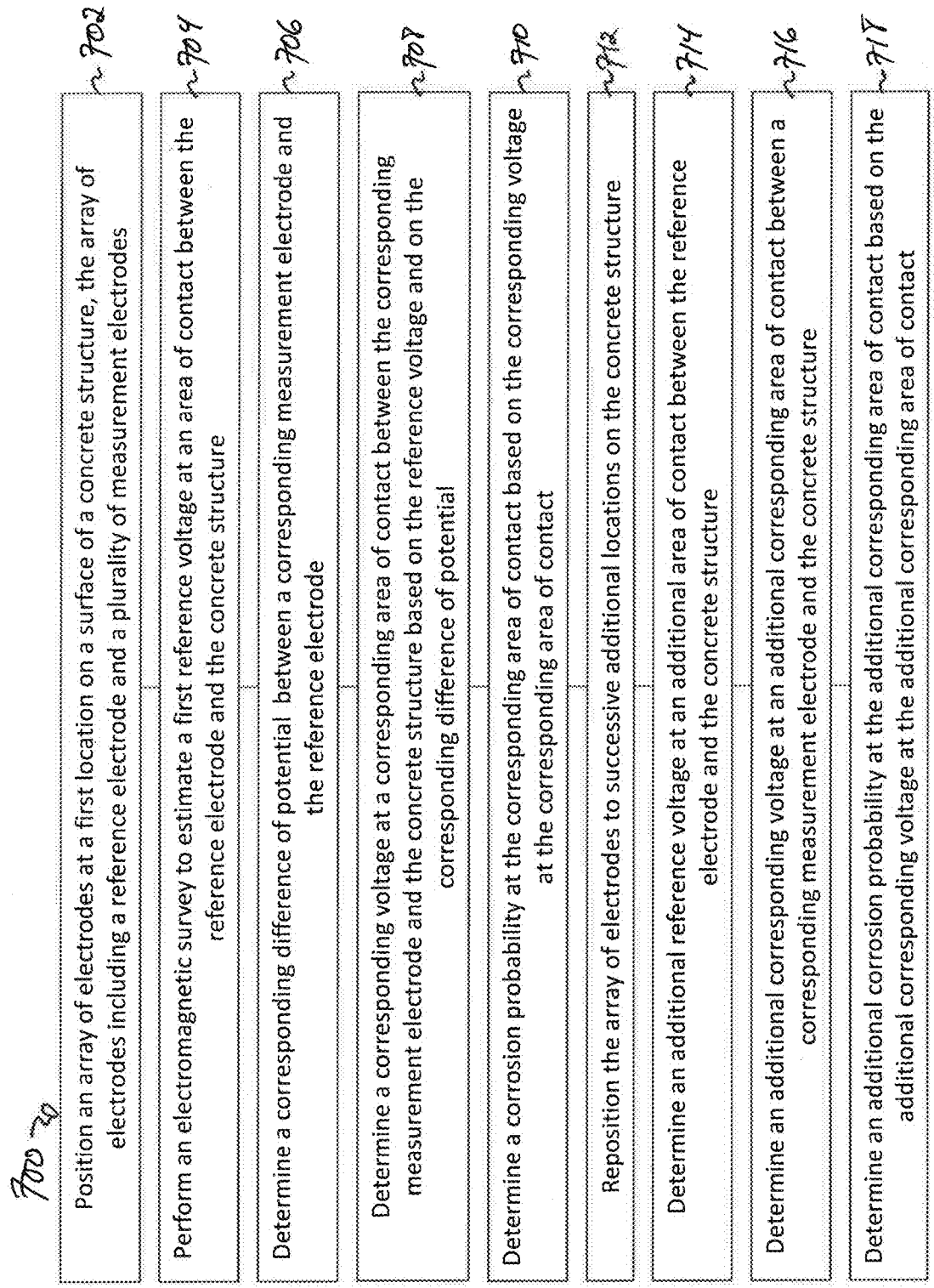
FIG. 14 is a flowchart of a second method for evaluating a condition of steel reinforcements in concrete.

FIG. 14 is a flowchart of a second method for evaluating a condition of steel reinforcements in concrete. A sequence 700 includes a plurality of operations, some of which may be executed in different orders, some of which are optional. The operations are as follows:

Operation 702: An array of electrodes is positioned at a first location on a concrete structure, for example on a surface of the concrete structure or on a surface of an asphalt overlay, if present, the array of electrodes including a reference electrode and a plurality of measurement electrodes.

Operation 704: An electromagnetic survey is performed in order to estimate first reference voltage V(Re) at an area of contact between the reference electrode and the concrete structure. The reference voltage is set to a high or low value in the same manner as expressed in the foregoing description of FIG. 12, Operation 606.

Operation 706: A corresponding difference of potential U is determined between the reference electrode and a corresponding measurement electrode Operation 708: A corresponding voltage V(i) at a corresponding area of contact between the corresponding measurement electrode and the concrete structure is determined based on the reference voltage V(Re) and on the corresponding difference of potential U.

Operation 710: A corrosion probability is determined at each corresponding area of contact based on the corresponding voltage V(i) at the corresponding area of contact. The corrosion probability is determined in the same manner as expressed in the foregoing description of FIG. 12, Operation 614.

Operation 712: The array of electrodes is repositioned to successive additional locations on the concrete structure, following which operations 714, 716 and 718 are repeated for each successive additional location of the array of electrodes on the concrete structure.

Operation 714: An additional reference voltage V(Re) at an additional area of contact between the reference electrode and the concrete structure is determined.

Operation 716: An additional corresponding voltage V(i) at an additional corresponding area of contact between a corresponding measurement electrode and the concrete structure is determined.

Operation 716: An additional corrosion probability is determined at each additional corresponding area of contact based on the additional corresponding voltage V(i) at the corresponding area of contact.

Figure 15:
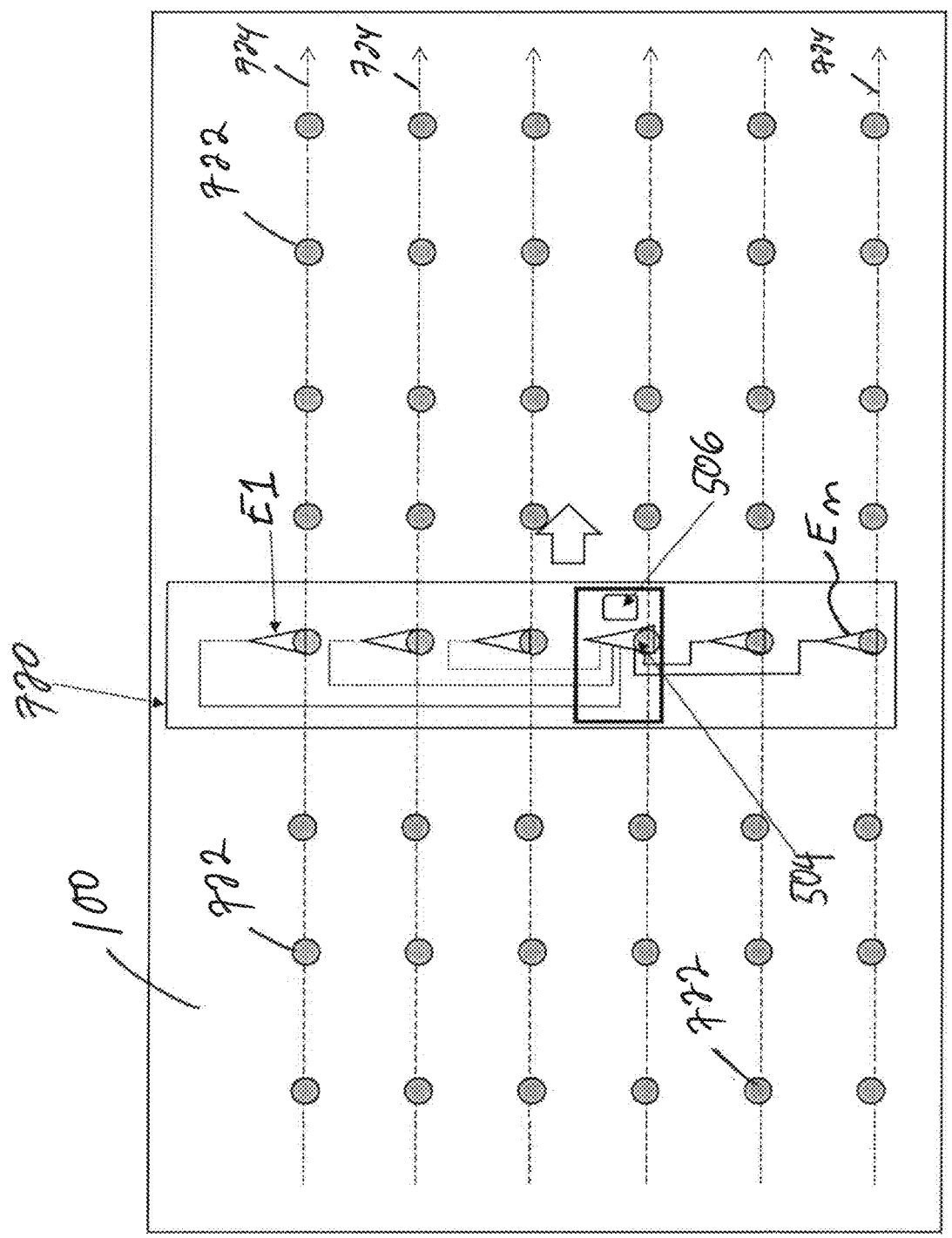
FIG. 15 is a top plan view of a concrete structure illustrating the method of 14.

FIG. 15 is a top plan view of a concrete structure illustrating the method of 14. An array 720 comprising the reference electrode 504, the EM sound unit 506 and the measurement electrodes E1-En is positioned on the concrete structure 100. The array 720 is moved along a length of the concrete structure 100 so that each of the electrodes 504 and E1-En successively passes over a measurement location 722 along arrows 724.

Those of ordinary skill in the art will realize that the description of the method, system and electrode for evaluating a condition of steel reinforcements in concrete are illustrative only and are not intended to be in any way limiting. Other embodiments will readily suggest themselves to such persons with ordinary skill in the art having the benefit of the present disclosure. Furthermore, the disclosed method, system and electrode may be customized to offer valuable solutions to existing needs and problems related to the detection of rebar corrosion in concrete structures. In the interest of clarity, not all of the routine features of the implementations of method, system and electrode are shown and described. In particular, combinations of features are not limited to those presented in the foregoing description as combinations of elements listed in the appended claims form an integral part of the present disclosure. It will, of course, be appreciated that in the development of any such actual implementation of the method, system and electrode, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of non-destructive testing of concrete structures having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer, a processor operatively connected to a memory, or a machine, those operations may be stored as a series of instructions readable by the machine, processor or computer, and may be stored on a non-transitory, tangible medium.

Systems and modules described herein may comprise software, firmware, hardware, or any combination(s) of software, firmware, or hardware suitable for the purposes described herein. Software and other modules may be executed by a processor and reside on a memory of servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

What is claimed is:

1. A method for evaluating a condition of steel reinforcements in a concrete structure, comprising:
positioning a reference electrode on a first area on the concrete structure;
performing an electromagnetic survey at the first area to estimate a reference voltage for the reference electrode;
positioning a measurement electrode on a second area on the concrete structure;
determining a difference of potential between the reference electrode and the measurement electrode;
determining a voltage at the measurement electrode based on the reference voltage and on the difference of potential; and
determining a corrosion probability at the second area based on the voltage at the measurement electrode.

2. The method of claim 1, wherein:
positioning the reference electrode on the first area of the concrete structure comprises positioning the reference electrode on a surface of the concrete structure; and
positioning the measurement electrode on the second area of the concrete structure comprises positioning the reference electrode on the surface of the concrete structure.

3. The method of claim 1, wherein the reference voltage has a high value for a low steel reinforcement corrosion probability and a low value less than the high value for a high steel reinforcement corrosion probability.

4. The method of claim 3, wherein:
a high corrosion probability is determined at the second area if the reference voltage has a first value and the voltage at the second area is less than a sum of the reference voltage plus a first predetermined threshold;
a low corrosion probability is determined at the second area if the reference voltage has a second value greater than the first value and the voltage at the second area is more than the reference voltage minus a second predetermined threshold;
a high corrosion probability is determined at the second area if the reference voltage has a third value and the voltage at the second area is lower than the reference voltage by at least a third predetermined threshold; and
a low corrosion probability is determined at the second area if the reference voltage has a fourth value less than the third value and the voltage at the second area is higher than the reference voltage by at least a fourth predetermined threshold.

5. The method of claim 4, wherein:
the high value of the reference voltage is about −150 mV;
the low value of the reference voltage is about −400 mV;
the first and second predetermined thresholds are about 50 mV; and the third and fourth predetermined thresholds are about 200 mV.

6. The method of claim 1, further comprising:
repositioning the measurement electrode to successive additional areas;
determining successive differences of potential between the reference electrode and the measurement electrode at each of the successive additional areas;
determining successive voltages at the measurement electrode based on the reference voltage and on the successive differences of potential; and
determining a corresponding corrosion probability at each of the successive additional areas based on a corresponding voltage at the measurement electrode.

7. The method of claim 1, further comprising:
positioning a plurality of additional measurement electrodes on a corresponding plurality of additional areas of the concrete structure, the measurement electrode and the additional measurement electrodes forming an electrode array, the second area and the additional areas forming an array of areas on the concrete structure;
using the electrode array to determine a corresponding voltage at each area of the array of areas; and
determining a corresponding corrosion probability at each area of the array of areas based on the corresponding voltage at each area of the array of areas.

8. The method of claim 7, further comprising:
repositioning the electrode array to successive additional arrays of areas;
using the electrode array to determine a corresponding voltage at each area of the successive additional arrays of areas; and
determining a corresponding corrosion probability at each area of the successive additional arrays of areas based on the corresponding voltage at each area of the array of areas.

9. A method for evaluating a condition of steel reinforcements in a concrete structure, comprising:
positioning an array of electrodes at a first location of the concrete structure, the array of electrodes including a reference electrode and a plurality of measurement electrodes;
performing an electromagnetic survey to estimate a first reference voltage at an area of contact between the reference electrode and the concrete structure;
for each of the plurality of measurement electrodes:
determining a corresponding difference of potential between the reference electrode and a corresponding measurement electrode;
determining a corresponding voltage at a corresponding area of contact between the corresponding measurement electrode and the concrete structure based on the reference voltage and on the corresponding difference of potential; and
determining a corresponding corrosion probability at the corresponding area of contact based on the corresponding voltage at the corresponding area of contact.

10. The method of claim 9, wherein:
positioning the array of electrodes at a first location of the concrete structure comprises positioning the array of electrodes on a surface of the concrete structure.

11. The method of claim 9, further comprising:
repositioning the array of electrodes to successive additional locations on the concrete structure; and
at each successive additional location of the array of electrodes on the concrete structure:
determining an additional reference voltage at an additional area of contact between the reference electrode and the concrete structure,
determining an additional corresponding voltage at an additional corresponding area of contact between each corresponding measurement electrode and the concrete structure, and
determining an additional corrosion probability at each additional corresponding area of contact based on the additional corresponding voltage at the additional corresponding area of contact.

12. A system for evaluating a condition of steel reinforcements in a concrete structure, comprising:
a reference electrode positionable on a first area of the concrete structure, the reference electrode comprising an electromagnetic sound unit;
a measurement electrode positionable on a second area of the concrete structure;
a voltmeter operatively connected to the reference electrode and to the measurement electrode and adapted to determine a difference of potential between the reference electrode and the measurement electrode; and
a processing unit operatively connected to the reference electrode and to the voltmeter, the processing unit being adapted to:
perform an electromagnetic survey of the first area based on measurements from the electromagnetic sound unit,
estimate a reference voltage for the reference electrode based on the electromagnetic survey,
determine a voltage at the measurement electrode based on the reference voltage and on the difference of potential, and
determine a corrosion probability at the second area based on the voltage at the measurement electrode.

13. The system of claim 12, further comprising an electrode array comprising the measurement electrode and a plurality of additional measurement electrodes.

14. The system of claim 12, further comprising an electrode array comprising the reference electrode, the measurement electrode and a plurality of additional measurement electrodes.

15. The system of claim 13, wherein the electrodes of the electrode array are mounted on rollable supports, whereby the electrode array is moveable on the concrete structure.

16. The system of claim 12, wherein the reference electrode is positionable on a surface of the concrete structure.

17. The system of claim 16, wherein:
the reference electrode comprises two wheels, a first wheel including the electromagnetic sound unit, a second wheel including a half-cell electrode placeable in electrolytic contact with the surface of the concrete structure; and
the measurement electrode comprises a wheel including a half-cell electrode placeable in electrolytic contact with the surface of the concrete structure.

18. An electrode for performing an electromagnetic survey on a concrete structure, comprising:
a first wheel including an electromagnetic sound unit; and
a second wheel mounted for rotating with the first wheel, the second wheel including a half-cell electrode placeable in electrolytic contact with a surface of the concrete structure.

19. The electrode of claim 18, further comprising a watertight bulkhead placed between the first and second wheels.

20. The electrode of claim 18, wherein the electromagnetic sound unit comprises:
- a transmitting antenna;
- a receiving antenna;
- a control unit operatively connected to the transmitting and receiving antennas; and
- a signaling link operatively connected to the control unit being adapted to exchange electromagnetic signals between an external processing unit and the transmitting and receiving antennas.

21. The electrode of claim 18, wherein second wheel further comprises a reservoir adapted to contain a conductive solution and to deliver the conductive solution for placing the half-cell electrode in electrolytic contact with the surface of the concrete structure.

* * * * *